United States Patent [19]
Richardson et al.

[11] Patent Number: 6,042,849
[45] Date of Patent: Mar. 28, 2000

[54] UNIT DOSAGE FORMS FOR TREATMENT OF VASOCONSTRICTION AND RELATED CONDITIONS

[75] Inventors: Kenneth T. Richardson, Anchorage, Ak.; Don C. Pearson, Tacoma, Wash.

[73] Assignee: ChronoRX, LLC, Anchorage, Ak.

[21] Appl. No.: 09/111,055

[22] Filed: Jul. 7, 1998

Related U.S. Application Data

[63] Continuation of application No. 08/849,068, filed as application No. PCT/US97/04286, Mar. 18, 1997, Pat. No. 5,849,338, and a continuation-in-part of application No. 08/753,967, Dec. 4, 1996, abandoned
[60] Provisional application No. 60/015,115, Apr. 10, 1996.
[51] Int. Cl.$^7$ ........................ A61K 31/355; A61K 31/34; A61K 33/06; A61K 33/04; A61K 31/495; A61K 31/50; A61K 31/40
[52] U.S. Cl. .......................... 424/682; 424/702; 514/249; 514/419; 514/458; 514/474; 514/929
[58] Field of Search ................................... 424/682, 702; 514/249, 419, 458, 474, 929

[56] References Cited

FOREIGN PATENT DOCUMENTS 2 057 463 6/1993 Canada .

OTHER PUBLICATIONS

B.M. Altura et al., "Magnesium in Cardiovascular Biology," *Science and Medicine (Scientific American)* (1995) 2(3): 28–37.
L.R. Barlow–Walden et al., "Melatonin Stimulates Brain Glutathione Peroxidase Activity," *Neurochemistry International* (1995) 26(5): 497–502.
F. Corica et al., "Effects of Oral Magnesium Supplementation of Plasma Lipid Concentrations in Patients with Non-–Insulin–Dependent Diabetes Mellitus," *Magnesium Research* (1994) 7(1): 43–47.
J.J. Cunningham et al., "Vitamin C: An Aldose Reductase Inhibitor that Normalizes Erythrocyte Sorbitol in Insulin–Dependent Diabetes Mellitus," *J. Am. Coll. Nutr.* (1994) 13(4): 344–350.
J. Durlach et al., "Magnesium and Ageing. II. Clinical Data: Aethiological Mechanisms and Pathophysiological Consequences of Magnesium Deficit in the Elderly," *Magnesium Research* (1993) 6(4): 379–393.
J. Flammer, "To What Extent are Vascular Factors Involved in the Pathogenesis of Glaucoma?," *Ocular Blood Flow* (1995) 1: 13–39.
A.Z. Gaspar et al., "The Influence of Magnesium on Visual Field and Peripheral Vasospasm in Glaucoma," *Ophthalmologica* (1995) 209:11–13.

I.O. Haeffliger et al., "The Vascular Endothelium as a Regulator of the Ocular Circulation: A New Concept in Ophthalmology?," *Survey of Ophthalmology* (1994) 39(2): 123–132.
J. Ma et al., "Associations of Serum and Dietary Magnesium with Cardiovascular Disease, Hypertension, Diabetes, Insulin, and Carotid Arterial Wall Thickness: The ARIC Study," *J Clin Epidermoil* (1995) 48(7): 927–940.
A. Mezzetti et al., "Vitamins E, C and Lipid Peroxidation in Plasma and Arterial Tissue of Smokers and Non–Smokers," *Atherosclerosis* (1995) 112: 91–99.
C. Pieri et al., "Melatonin: A Peroxyl Radical Scavenger More Effective Than Vitamin E," *Life Sciences* (1994) 55(15): 271–276.
Y. Rayssiguier et al., "Magnesium and Ageing. I. Experimental Data: Importance of Oxidative Damage," *Magnesium Research* (1993) 6(4): 369–378.
R.J. Reiter et al., "A Review of the Evidence Supporting Melatonin's Role as an Antioxidant," *J. Pineal Res* (1995) 18:1–11.
G.T. Vatassery, "In Vitro Oxidation of Vitamins C and E, Cholesterol, and Thiols in Rat Brain Synaptosomes," *Lipids* (1995) 30(11): 1007–1013.
J. White Jr. et al., "Magnesium and Diabetes: A Review," *The Annals of Pharmacotherapy* (1993) 27: 775–780.
Facts and Comparisons, J.B. Lippincott Co., pp. 1–2a, 24, 33a, 1992.
CA 124:20800, Zidek, 1993.
CA 120:95292, Mirzoyan et al, 1993.
CA 96:51091, Yoon et al, 1981.
CA 71:100350, Kopjas, 1969.
CA 122:212713, Han et al, 1994.

*Primary Examiner*—Kimberly Jordan
*Attorney, Agent, or Firm*—Townsend and Townsend and Crew LLP

[57] ABSTRACT

Magnesium is formulated in combination with vitamin E, vitamin C, folate, selenium, and optionally melatonin a unit dosage form for oral administration, for the treatment of vasoconstriction and the physiological and pathological conditions giving rise to vasoconstriction. These active agents complement each other in suppressing these conditions, using a variety of mechanisms operating in conjunction with one another. The inclusion of magnesium in a plurality of forms provides additional advantages in terms of controlling and sustaining the release of magnesium in locations along the digestive tract where the magnesium will have its greatest effectiveness as a therapeutic agent, thus improving control over the clinical bioavailability of magnesium and in improving the selection of appropriate therapeutic ranges.

21 Claims, No Drawings

UNIT DOSAGE FORMS FOR TREATMENT OF VASOCONSTRICTION AND RELATED CONDITIONS

CROSS REFERENCE TO RELATED APPLICATION

This application is a continuation of and claims the benefit of U.S. patent application Ser. No. 08/849,068, filed Aug. 26, 1997, now U.S. Pat. No. 5,849,338, which is the United States national phase of international PCT application Ser. No. PCT/US97/04286, filed Mar. 18, 1997, which is a continuation-in-part of U.S. patent application Ser. No. 08/753,967, filed Dec. 4, 1996, now abandonded. Both applications are related to U.S. Provisional Patent Application Ser. No. 60/015,115, filed Apr. 10, 1996, and claim benefit therefrom for all legal purposes to be served thereby. The disclosures of application Ser. No. 60/015,115, filed Apr. 10, 1996, and application Ser. No. 08/753,967, filed Dec. 4, 1996, are incorporated herein by reference.

BACKGROUND OF THE INVENTION

1. Field of the Invention

This invention is in the field of pharmacology, and relates specifically to the pharmacological treatment of conditions associated with the constriction of small blood vessels.

2. Description of the Prior Art

Vasoconstriction, or the reduction in the cross-sectional area of the lumen of small blood vessels, is a potentially lethal condition arising in a variety of pathologies, and is due either to vasospasm, inadequate vasodilatation, thickening of the vessel wall, or the accumulation of flow-restricting materials on the internal wall surfaces or within the wall itself. Vasoconstriction is a major factor in various diseases, including progressive generalized atherogenesis, heart attack, stroke, hypertension, glaucoma, migraine, hypertension of pregnancy, and diabetes mellitus, among others.

Vasoconstriction originates in a variety of ways. One example is the local conversion by dysfunctional endothelium of circulating low density lipoproteins (LDL) into oxidatively activated low density lipoproteins ((ox)LDL). (ox)LDL is internalized via cellular macrophage scavenger receptors creating lipid-engorged macrophages, called "foam cells." These cells are bound to the vascular endothelium and subendothelium, release a variety of growth factors and cytokines that stimulate vascular smooth muscle cell proliferation and trigger the increase of the local endothelial expression of leukocyte adhesion molecules and leukocyte chemoattractants; all precursors of progressive vascular atherosclerosis and its subsequent reduction of vascular cross-sectional area.

Another example is the endothelial cell release of endothelin-1, a powerful arterial vasoconstrictor. Repetitive or prolonged vasospasm results in mechanical hypertrophy, proliferation of the microvascular smooth muscle fibers (hyperplasia), and a consequent secondary thickening of the vascular media wall. Various mechanisms leading to the release of endothelin-1 are known. These mechanisms include: its induction by the increase in availability of intracellular ionic calcium which results from the opening of calcium channels in dysfunctional endothelium; and its induction by the reactive sulfhydryl group of homocysteine which is released by endothelial cells that have been damaged by "foam cells."

A third example of vasoconstriction is the activation, rolling, local accumulation, and eventual cell-to-cell adhesion of platelets and white blood cells on the endothelial surface and within the subendothelium. This accumulation stimulates the platelets to activate and attract those macrophages which will be converted into "foam cells," initiate smooth muscle cell proliferation, and release additional leukocyte chemoattractants. These events result in additive vasospastic and mechanical vascular blockade.

A fourth example is the conversion of glucose to sorbitol, which causes irregular vasoconstriction or vasodilatation due to the osmotically induced death of vascular pericytes in diabetes mellitus.

Magnesium is known to reduce the risk of vasoconstriction and also to influence a broad diversity of functions in physiology and pathology. In addition to improving adenosine triphosphate (cATP) energy-requiring metabolism and anaerobic phosphorylation, magnesium suppresses the conversion of LDL to (ox)LDL, reduces platelet and white blood cell aggregation and adhesion, and serves as a physiological calcium channel blocker, thereby reducing the production of endothelin-1 by atherosclerotic endothelial cells. Its action in improving cATP and prostacyclin synthesis of EDRF (Endothelial Derived Relaxation Factor—otherwise referred to as nitric oxide), reduces vasoconstriction by actively inducing vasorelaxation.

The recommended daily allowance of ionic magnesium for humans is 350 mg. Magnesium deficiencies have been documented in many segments of the world population. It is estimated that the average adult in Western society has a dietary magnesium shortfall of 90–178 mg per day. This fundamental deficiency is more clearly serious in those who already suffer from atherosclerosis, primary vasospastic vasculopathies or other diseases with a vasospastic component. Ionic magnesium deficiencies are particularly prevalent among diabetics with normal renal function, alcoholics, smokers, the elderly, and those who suffer from a variety of gastrointestinal motility or absorption disorders.

Ionic magnesium in mammals resides in three compartments: (1) in bone; (2) in an intracellular bound form (for example, in ionic linkage with an anionic substrate) or an intracellular unbound form; and (3) in circulating bound and unbound forms. When the concentration of circulating magnesium in the bloodstream increases as a result of the dietary uptake of magnesium, the body quickly responds by sequestering the magnesium into one of the bound or intracellular forms listed above. If elemental magnesium is ingested in a bulk amount which results in the absorption of a magnesium bolus in excess of 8 mEq, the renal excretion of magnesium rapidly increases and, as a result, becomes less efficient in the resorption of this element. Thus, the accurate sustenance of an appropriate magnesium level requires the repeated administration of carefully designed ionic-magnesium-containing medicaments with correctly formulated, absorption targeted amounts.

At the present time, a sustained elevation of magnesium can be attained only by the repeated consumption of a bewildering variety of magnesium-containing tablets. Unfortunately, available products are frequently either unclear or inaccurate in specifying their formulation or in specifying the amount of ionic magnesium they provide, or they make available ionic magnesium in amounts below or above the ideal (frequently greatly below or above appropriate levels). For these reasons, it has proved clinically difficult rationally to administer elemental magnesium in a manner permitting it to achieve its full potential as therapy for the control of vasoconstriction and the various diseases and conditions giving rise to or otherwise associated with vasoconstriction. This invention, by virtue of its careful selection of appropriate components with complementary therapeutic effects, delivered at specified dosage levels targeted for suitable gastrointestinal absorption, eliminates the current confusion about correct product selection and the frequent clinical use of inappropriate doses.

SUMMARY OF THE INVENTION

The present invention resides in a pharmaceutical preparation for use as an oral dosage form. The preparation contains ionic magnesium combined with additional therapeutic substances in an interactive and complementary manner for the treatment and control of vasoconstriction and of the physiological conditions that give rise to vasoconstriction. The additional therapeutic substances are: (a) vitamin E or its analogs, (b) vitamin C or its analogs, (c) folic acid or folate ion, and (d) selenium. Certain embodiments of this invention further contain melatonin as an additional therapeutic substance. The vitamin E component is either α-tocopherol, β-tocopherol, esters of α- or β-tocopherol, or combinations of these species. Examples of esters of the tocopherols are acetate and succinate esters. The vitamin C component is either ascorbic acid, a salt with ascorbate ion as the anion, or a combination of the two. In preferred embodiments, the ionic magnesium component consists of one or more magnesium salts of limited water solubility, and more preferably a combination of magnesium salts each having a different water solubility.

As a unit dosage, the preparation is administered in a uniquely efficient form with each of its components in amounts appropriate to complement each other in producing an overall beneficial biological effect. For example, vitamin C blocks the oxidative activation of LDL to (ox)LDL, and does so in conjunction with vitamin E with which it acts as a coantioxidant. Vitamin E produces antioxidant effects with regard to LDL oxidation. Vitamin E also suppresses the formation of (ox)LDL by combining with LDL in the liver to form the complex E-LDL which is resistant to oxidation. Following these antioxidant activities, Vitamin E is reconstituted into an effective antioxidant by vitamin C or by selenium. In consequence, deficiencies of ascorbate and/or selenium result in a corresponding reduction in vitamin E.

Magnesium and melatonin both suppress LDL oxidation, each thereby acting in a complementary manner relative to these actions of vitamins C and E. Vitamin E and selenium form a synergistic mechanism for antioxidant defense. Selenium is an essential component of glutathione peroxidase (GSH-Px), and selenium and vitamin E together decompose fatty acid hydroperoxides and hydrogen peroxides generated by free radical reactions. Both types of peroxides are associated with the vasoconstriction that accompanies free radical damage of the vascular endothelial cells. Vitamin C suppresses the patchy irregularity of unpredictable diabetic vasoconstriction and vasodilatation, caused by sorbitol induced pericytic death by inhibiting the enzyme aldose reductase which is involved in the conversion of excess glucose to sorbitol. In addition, magnesium reduces vasoconstriction by the mechanism of calcium channel blockade. Calcium channel blockade interferes with the $Ca^{++}$-dependent, rate-limited endothelial production of the vasoconstrictor, endothelin-1. By reducing this dysfunctional endothelial intracellular $Ca^{++}$ ingress, calcium channel blockade also negatively influences $Ca^{++}$-dependent platelet aggregation and granulation, and white blood cell aggregation and adhesion.

In preparations that include melatonin, melatonin maintains cholesterol homeostasis by enhancing the catabolism of cholesterol to bile acids and by reducing cholesterol synthesis via inhibition of the pathway between lanosterol (a cholesterol precursor) and cholesterol, leading to a reduction in the total cholesterol with an improvement in the HDL/LDL ratio. Melatonin also reduces the toxic peroxyl and hydroxyl radicals derived from $H_2O_2$. Melatonin is also an effective antioxidant and has an affinity for α-2 adrenoreceptors thereby modulating the α-2 agonists implicated in vasoconstriction. A further feature of melatonin is that it appears to act as a natural calcium channel blocker by inhibiting cellular $Ca^{++}$ influx through voltage-sensitive channels. Melatonin-containing formulations are of particular usefulness for subjects with reduced melatonin levels. Such reduced levels occur as individuals age and are universally prevalent in the elderly. Melatonin-containing formulations are generally useful for subjects that would benefit from an increased melatonin level.

In addition to suppressing vasoconstriction, the dosage form of the invention actively promotes vasorelaxation. This is achieved by both ionic magnesium and vitamin E, again in complementary fashion. Ionic magnesium is required by the cATP and prostacyclin synthesis of (EDRF) nitric oxide, while vitamin E promotes the ACh/cATP (acetylcholine/cyclic adenosine triphosphate) synthesis of EDRF (Endothelium Derived Relaxation Factor).

In preferred embodiments of the invention, the pharmaceutical preparation is formulated to release magnesium ion at various appropriate locations along the digestive tract, i.e., within the stomach as well as the intestine, and preferably within both the mid-proximal and the distal small intestine, although not in the colon. The release of magnesium is thus directed to regions where maximal absorption will occur, the ileum and jejunum, while minimizing laxative effects in the colon. Distributive release avoids "bolus" dumping of elemental magnesium by the kidneys. Other features of preferred embodiments include formulating the preparation in a manner that will contain and release appropriate amounts of ionic magnesium in an oral dosage form with the least bulk while still achieving site-specific and controlled release effects.

These and other features and advantages of the invention will become apparent and be better understood from the description that follows.

DETAILED DESCRIPTION OF THE INVENTION AND PREFERRED EMBODIMENTS

Definitions

All terms appearing in this specification and the appended claims are used in the same manner as commonly recognized among those skilled in the technology and terminology of pharmacology. These terms are therefore used in accordance with their conventional definitions, except as otherwise noted. Further clarifications of some of these terms as they apply specifically to this invention are offered below.

"Unit dosage form" refers to a composition intended for a single administration to treat a subject suffering from a disease or medical condition. Each unit dosage form typically comprises each of the active ingredients of this invention plus pharmaceutically acceptable excipients. Examples of unit dosage forms are individual tablets, individual gelatin capsules, bulk powders, and liquid solutions, emulsions or suspensions. Treatment of the disease or condition may require periodic administration of unit dosage forms, for example: one unit dosage form two or more times a day, one with each meal, one every four hours or other interval, or only one per day. The expression "oral unit dosage form" indicates a unit dosage form designed to be taken orally.

Persons suffering from "magnesium deficiency" are those who consume less than the recommended daily allowance of ionic magnesium (350 mg) or who exhibit an abnormal condition that is treatable by the administration of magnesium.

An "active agent" or "active ingredient" is a component of a dosage form that performs a biological function when administered or induces or affects (enhances or inhibits) a physiological process in some manner. "Activity" is the ability to perform the function, or to induce or affect the process. Active agents and ingredients are distinguishable from excipients such as carriers, vehicles, diluents, lubricants, binders, and other formulating aids, and encapsulating or otherwise protective components.

"Delivery vehicle" is a composition which comprises one or more active agents, and is designed to release the active agent in a particular fashion, either by immediately dispersing the agents in the digestive system, or by releasing the agents in a slow sustained fashion. The term encompasses porous microspheres, microcapsules, cross-linked porous beads, and liposomes that contain one or more active ingredients sequestered within internal cavities or porous spaces. The term also includes osmotic delivery systems, coated tablets or capsules that include nonporous microspheres, microcapsules, and liposomes, and active agents dispersed within polymeric matrices. A dosage form can include one or more delivery vehicles.

"Controlled" or "sustained" or "time release" delivery are equivalent terms that describe the type of active agent delivery that occurs when the active agent is released from a delivery vehicle at an ascertainable and manipulatable rate over a period of time, which is generally on the order of minutes, hours or days, typically ranging from about thirty minutes to about 3 days, rather than being dispersed immediately upon entry into the digestive tract or upon contact with gastric fluid. A controlled release rate can vary as a function of a multiplicity of factors. Factors influencing the rate of delivery in controlled release include the particle size, composition, porosity, charge structure, and degree of hydration of the delivery vehicle and the active ingredient(s), the acidity of the environment (either internal or external to the delivery vehicle), and the solubility of the active agent in the physiological environment, i.e., the particular location along the digestive tract.

"Targeted" or "site-specific" delivery means that the pharmaceutical preparation is formulated to limit the release of its contents in an amount appropriate to the site where release occurs. The term refers in particular to the active agent, whose site-specific delivery implements the performance of the therapeutic function at a specific site within the body of the subject to whom the preparation is administered.

The phrase "therapeutically effective amount" means an amount sufficient to produce a therapeutic result. Generally the therapeutic result is an objective or subjective improvement of a disease or condition, achieved by inducing or enhancing a physiological process, blocking or inhibiting a physiological process, or in general terms performing a biological function that helps in or contributes to the elimination or abatement of the disease or condition.

"Vasoconstriction" is the reduction of the cross section of a blood vessel lumen, inhibiting the free flow of blood through the vessel. Vasoconstriction can arise from vasospasm, deposits on or in the lumen wall or from the thickening of the wall material due to excessive growth or proliferation of one or more of the wall layers.

"Low density lipids," "low density lipoproteins," and "LDL" refer generally to spheroidal, apolipoprotein-containing plasma lipoproteins having densities in the range of about 1.006 to about 1.063 g/mL. LDL contain about 22% protein, 22% phospholipid, 46% cholesterol and cholesterol esters, and 10% triglycerides.

The phrase "substantially homogeneous," when used to describe a formulation (or portion of a formulation) that contains a combination of components, means that the components, although each may be in particle or powder form, are fully mixed so that the individual components are not divided into discrete layers or form concentration gradients within the formulation.

Compositions, Formulations and Dosages

The amounts of the individual components of the pharmaceutical preparation of this invention can vary, although in preferred preparations the components are present in amounts lying within certain ranges. Expressed both in terms of milligrams and in terms of weight ratios relative to atomic magnesium, the components and their preferred ranges are as follows:

TABLE I

| Component | Ranges (approximate) | | Ranges in Weight Ratios Relative to Magnesium (approximate) | |
| --- | --- | --- | --- | --- |
| | Preferred | Most Preferred | Preferred | Most Preferred |
| Magnesium (as atomic magnesium) | 20 to 700 mg | 40 to 180 mg | — | — |
| Vitamin E and/or analogs | 15 to 1,000 IU | 20 to 400 IU | 0.2:1 to 2:1 | 0.5:1 to 1:1 |
| Vitamin C and/or analogs | 30 to 1,000 mg | 40 to 500 mg | 0.2:1 to 2:1 | 0.5:1 to 1:1 |
| Melatonin and/or analogs | 0.1 to 40 mg | 0.5 to 30 mg | 0.03:1 to 0.3:1 | 0.1:1 to 0.2:1 |
| Folic Acid | 0.05 to 0.225 mg | 0.10 to 0.20 mg | 0.0003:1 to 0.0030:1 | 0.00075:1 to 0.0020:1 |
| Selenium | 0.005 to 0.15 mg | 0.005 to 0.035 mg | 0.00011:1 to 0.00043:1 | 0.0009:1 to 0.0036:1 |

As stated above, the ionic magnesium is present either as magnesium salts, other magnesium compounds that release magnesium ion when ingested, or both. Examples of forms of magnesium that can be used in this invention are magnesium lactate, magnesium citrate, magnesium stearate, magnesium acetate, magnesium ascorbate, magnesium taurate, magnesium malate, magnesium orotate, magnesium diglycinate and magnesium oxide. Magnesium citrate is soluble in gastric fluid and thus is readily available for passive absorption in the upper gastrointestinal tract. The citrate radical offers the added benefit of reducing renal calculi. Magnesium and taurine act in a complementary way to improve insulin sensitivity and act in a parallel manner to reduce vasoconstriction, reduce atherogenesis and stabilize platelets. Magnesium acetate, magnesium ascorbate and magnesium lactate are also soluble in gastric fluid and share the upper gastrointestinal passive absorption potential of magnesium citrate. The ascorbate radical serves as a source of vitamin C by conversion to ascorbic acid upon exposure to hydrochloric acid in the gastric fluid, while the magnesium ion is converted to soluble magnesium chloride. The satisfactory water solubility of magnesium acetate, magnesium ascorbate, magnesium citrate and magnesium lactate provide for a diffusional gradient of magnesium in the upper small intestine where some passive absorption of magnesium occurs. The variable water solubilities of the magnesium salts provide for flexibility in the time and location profile of sustained release from hydrophilic polymeric matrices. Magnesium oxide is converted to magnesium chloride in the stomach, and offers the advantage of a high ionic magnesium content, since 60% by weight of the magnesium oxide molecule is atomic magnesium. Magnesium diglycinate (chelate) represents a form of magnesium that is absorbed in part as an intact dipeptide in the proximal small intestine via a dipeptide transport pathway and therefore provides a third absorptive mechanism for magnesium. Magnesium stearate is useful as a lubricant when compressing the composition into tablets, in addition to its use as a minor magnesium source. A preferred combination of magnesium sources is magnesium citrate and magnesium ascorbate; another preferred combination is magnesium diglycinate, magnesium ascorbate, magnesium citrate, and magnesium oxide; and still another preferred combination is magnesium taurate, magnesium citrate, magnesium ascorbate, and magnesium oxide.

Preferred among vitamin E and its analogs and esters are a-tocopherol, α-tocopherol acid succinate, and α-tocopherol acetate. A particularly preferred form of vitamin E is α-tocopherol acid succinate, especially for preparations in tablet form.

While the vitamin C component can be included either as ascorbic acid or ascorbate ion, it is more efficiently and preferably supplied as magnesium ascorbate since this form supplies further magnesium.

The selenium component can be present as atomic selenium, but is preferably included as a selenium compound, organic or inorganic. Any selenium compound that is non-toxic at the levels administered, and capable of being formulated with the other components can be used. Examples of selenium compounds suitable for use herein are selenols such as methyl selenol and ethyl selenol, selenophenols such as selenophenol itself, and alkali or alkaline earth metal selenites, such as sodium selenite.

When melatonin is to be included, either melatonin itself or its analogs can be used. Examples of analogs are serotonin and indole-3-acetic acid. Other analogs will be known to those skilled in the art.

Additional active agents are optionally included in the formulations of this invention for the treatment of specific conditions or for use in specific patient populations. Examples are calcium and calcium salts (about 400 mg to about 1200 mg), optionally combined with vitamin D (about 1 µg to about 20 µg), for treating conditions in which hypomagnesemia adversely impacts calcium utilization; lycopene or other carotenoids as antioxidants; zinc salts (about 10 µg to about 100 µg) as antioxidants; and elemental iron (about 10 µg to about 100 µg) for anemic patients. Formulations specifically for use by diabetics can include additional substances such as chromium (picolinate or chromium complexes as in brewers yeast), zinc salts and complementary nutritional substances. Formulations specifically for use by senior citizens can include, in a variety of dosage forms, more expansive dietary supplements that typically are necessary for the aged, in a variety of dosage forms. Formulations specifically for use by participants in sports can include dietary supplements that are typically necessary for athletes. Formulations specifically for use by alcoholics, smokers, diabetics and institutionalized patients can include multivitamins and additional, complementary therapeutic substrates. Components of formulations for other specific uses or patient populations will be readily apparent to those skilled in the art.

A slower, more sustained release of the active agents can be achieved by placing the active agents in one or more delivery vehicles that inherently retard the release rate. Examples of such delivery vehicles are polymeric matrices that maintain their structural integrity for a period of time prior to dissolving, or that resist dissolving in the stomach but are readily made available in the post-gastric environment by the alkalinity of the intestine, or by the action of metabolites and enzymes that are present only in the intestine. The preparation and use of polymeric matrices designed for sustained drug release is well known. Examples are disclosed in U.S. Pat. No. 5,238,714 (Aug. 24, 1993) to Wallace et al.; Bechtel, W., *Radiology* 161: 601–604 (1986); and Tice et al., EPO 0302582, Feb. 8, 1989. Selection of the most appropriate polymeric matrix for a particular formulation can be governed by the intended use of the formulation. Preferred polymeric matrices are hydrophilic, water-swellable polymers such as hydroxymethylcellulose, hydroxypropylcellulose, hydroxyethylcellulose, hydroxymethylpropylcellulose, polyethylene oxide, and porous bioerodible particles prepared from alginate and chitosan that have been jonically crosslinked.

A delayed, post-gastric, prolonged release of the active ingredients in the small intestine (duodenum, ileum, jejunum) can also be achieved by encasing the active agents, or by encasing hydrophilic, water-swellable polymers containing the active agents, in an enteric (acid-resistant) film. One class of acid-resistant agents suitable for this purpose is that disclosed in Eury et al., U.S. Pat. No. 5,316,774 ("Blocked Polymeric Particles Having Internal Pore Networks for Delivering Active Substances to Selected Environments"). The formulations disclosed in this patent consist of porous particles whose pores contain an active ingredient and a polymer acting as a blocking agent that degrades and releases the active ingredient upon exposure to either low or high pH or to changes in ionic strength. The most effective enteric materials include polyacids having a $pK_a$ of from about 3 to 5. Examples of such materials are fatty acid mixtures, methacrylic acid polymers and copolymers, ethyl cellulose, and cellulose acetate phthalates. Specific examples are methacrylic acid copolymers sold under the name EUDRAGIT®, available from Rohm Tech, Inc., Maiden, Mass., USA; and the cellulose acetate phthalate latex AQUATERIC®, available from FMC Corporation, New York, N.Y., USA, and similar products available from Eastman-Kodak Co., Rochester, N.Y., USA.

Acid-resistant films of these types are particularly useful in confining the release of magnesium lactate and magnesium citrate to the post-gastric environment. Acid-resistant films can be applied as coatings over individual particles of the components of the formulation, with the coated particles then optionally compressed into tablets. An acid-resistant film can also be applied as a layer encasing an entire tablet or a portion of a tablet where each tablet is a single unit dosage form.

The dosage forms of the invention optionally include one or more suitable and pharmaceutically acceptable excipients, such as ethyl cellulose, cellulose acetate phthalates, mannitol, lactose, starch, magnesium stearate, sodium saccharin, talcum, glucose, sucrose, carbonate, and the like. These excipients serve a variety of functions, as indicated above, as carriers, vehicles, diluents, binders, and other formulating aids. In general, the dosage forms of this invention include powders, liquid forms, tablets or capsules.

In certain embodiments of the invention, the dosage form is a substantially homogeneous single layer tablet that releases all of its components into the stomach upon ingestion. An example of such a tablet is one that contains magnesium oxide, preferably in an amount of about 50 mg to about 150 mg; magnesium acetate, preferably in an amount of about 50 mg to about 100 mg; magnesium ascorbate, preferably in an amount of about 50 mg to about 100 mg (this will provide about 4 mg to about 8 mg of elemental magnesium and about 50 mg to about 100 mg of ascorbate); α-tocopherol succinate, preferably in an amount of about 50 IU to about 100 IU; folic acid, preferably in an amount of about 0.03 mg to about 0.3 mg; and sodium selenite, preferably in an amount of about 7.0 to about 20.0 micrograms. When magnesium citrate is included in this tablet, the preferred amount is about 30 mg to about 100 mg.

In certain other embodiments of the invention, the dosage form is a combination tablet in which the components are divided into two portions, one that is fully released into the stomach upon ingestion, and the other protected by an acid-resistant coating for release only in the intestine, and optionally in a sustained-release manner over a period of time. An example of such a tablet is one in which the stomach-release portion contains the vitamin E compound, preferably α-tocopherol acid succinate in an amount of about 50 IU to about 100 IU; either folic acid or folate ion, preferably in an amount of about 0.03 mg to about 0.3 mg; selenium in an amount of about 0.007 mg to about 0.20 mg; and various magnesium compounds, preferably magnesium oxide in an amount of about 50 mg to about 100 mg, magnesium diglycinate in an amount of about 50 mg to about 200 mg, and about 150 mg to about 250 mg of magnesium ascorbate. The intestine-release portion contains selected water-soluble magnesium compounds, preferably about 50 mg to about 100 mg of magnesium citrate and about 40 mg to about 100 mg of magnesium acetate.

The dosage forms of this invention can be formulated for administration at rates of either one unit dosage form per day, or two or more. Unit dosage forms to be taken one to four times per day are preferred.

The following examples are offered for purposes of illustration only.

EXAMPLE 1

A single layer tablet, substantially homogeneous in composition, which will disintegrate upon ingestion to provide simultaneous accessibility to all components, is prepared with the following composition:

TABLE II

| Component | Formula | weight (mg except where otherwise indicated) | weight % |
|---|---|---|---|
| Magnesium acetate (tetrahydrate) | $(CH_3COO)_2Mg \cdot 4H_2O$ | 67.67 | 13.86 |
| Magnesium ascorbate | $C_{12}H_{14}MgO_{12}$ | 64.17 | 13.14 |
| Magnesium citrate (pentahydrate) | $C_6H_5MgO_7 \cdot 5H_2O$ | 54.36 | 11.13 |
| Magnesium oxide (compressible) | MgO | 118.54 | 24.25 |
| Magnesium stearate | $Mg(C_{18}H_{35}O_2)_2$ | 3.55 | 0.73 |
| Vitamin E acid succinate | $C_{33}H_{54}O_5$ | 60 IU | 12.29 |
| Selenophenol or Selenomethanol | $C_6H_5SeH$ or $CH_3SeH$ | 0.10 | 0.02 |
| Melatonin | $C_{13}H_{16}N_2O_2$ | 0.1–40 | 0.02–8.0 |
| Folic acid | $C_{19}H_{19}N_7O_6$ | 0.20 | 0.04 |
| Starch | | 120.00 | 24.57 |

This tablet contains 88 mg elemental magnesium, 55 mg citrate ion, 60 IU vitamin E, and provides 60 mg of ascorbate. The tablet is coated with a coating that dissolves in an aqueous environment. Examples of such a coating are SURELEASE and OPADRY (both available from Colorcon, West Point, Pa., USA).

The tablet is made by weighing and mixing all ingredients together in a twin-shell blender, granulating either by roller compaction and milling or by a wet granulation process, and feeding the mixture into a high-speed, rotary tablet press. The starch is a tablet binder, for which lactose can be substituted if desired.

EXAMPLE 2

This example illustrates a dual layer tablet, with each layer substantially homogeneous in composition, including an immediate release layer that disintegrates in the stomach to provide simultaneous accessibility to all of the immediate release components and a controlled release layer that remains intact until reaching the intestine where it provides accessibility to all of its components. The tablet is prepared with the following composition:

TABLE III

| Immediate Release Layer | | | |
|---|---|---|---|
| Component | Formula | weight (mg, except where indicated) | weight % |
| Magnesium oxide (compressible) | MgO | 93.24 | 20.19 |
| Magnesium ascorbate | $C_{12}H_{14}MgO_{12}$ | 171.11 | 37.06 |
| Magnesium stearate | $Mg(C_{18}H_{35}O_2)_2$ | 2.19 | 0.47 |
| Vitamin E acid succinate | $C_{33}H_{54}O_5$ | 125 IU | 24.07 |
| Folic acid | $C_{19}H_{19}N_7O_6$ | 0.20 | 0.40 |
| Sodium selenite | $Na_2SeO_3$ | 0.01 | 0.002 |
| Starch | | 70.00 | 15.16 |
| Controlled Release Layer | | | |
| Component | Formula | weight (mg) | weight % |
| Magnesium acetate (tetrahydrate) | $(CH_3COO)_2Mg \cdot 4H_2O$ | 67.67 | 19.98 |

TABLE III-continued

| | | | |
|---|---|---|---|
| Magnesium citrate (pentahydrate) | $C_6H_5MgO_7.5H_2O$ | 163.07 | 48.14 |
| Melatonin | $C_{13}H_{16}N_2O_2$ | 3.00 | 0.89 |
| Water-soluble, cellulose-based polymer | | 105.00 | 20.72 |

The controlled release layer comprises 64% by weight of the tablet and has an acid-resistant coating separating it from the immediate release layer. The immediate release layer comprises 36% by weight of the tablet and has a coating that dissolves in an aqueous environment. The immediate release layer contains 56 mg magnesium, 0.2 mg folic acid, 125 IU vitamin E, and provides 0.01 mg of selenium, while the controlled release layer contains 32 mg elemental magnesium, 150 mg citrate, and 160 mg vitamin E.

Ingredients for each layer are fed into appropriate hoppers of a two-layer, rotary tablet press, and compressed into two-layer tablets. The magnesium stearate present in both layers provides lubrication of the tablet press and serves as a minimal source of magnesium in the formulation. Selenium and folic acid are each added as a spray.

Upon oral ingestion of the tablet, agents of the immediate release layer dissolve rapidly in the stomach and are available for immediate absorption in the gastrointestinal tract. The polymer matrix of the controlled release layer, having been given an enteric coating in the granulation process with EUDRAGIT, does not dissolve in the acid pH of the stomach, but remains intact until it passes to the upper part of the small intestine, where the enteric coating dissolves in the more alkaline environment of the intestine. The polymeric matrix then immediately begins to imbibe water from the intestinal fluid, forming a water-swollen gel. The agents incorporated into this layer are then available for intestinal absorption as they osmotically diffuse from the gel. Since the agents have been selected with a view toward their water solubilities, the rate of diffusion of each agent is reasonably constant for the useful life of the matrix (approximately four hours), by which time the incorporated agents are finally depleted and the matrix disintegrates.

Methods of Administration and Types of Utility

The compositions and dosage forms of the invention are useful for treating magnesium deficiencies, particularly in treating magnesium and metabolite deficiencies that are characteristic of specific segments of the population. Non-limiting examples are hypomagnesemics, junk food consumers, members of the general population who live in geographical areas with low elemental magnesium levels in the water or in dietary vegetables, alcoholics (who are often magnesium deficient and malnourished), the elderly (who are commonly deficient in both magnesium and folic acid), diabetics (except those suffering from renal failure), institutionalized patients, smokers, and persons afflicted with vasospastic vasculopathies.

The compositions of the present invention are particularly useful for reducing or controlling risk factors that are correlated with a high probability of developing or complicating certain disease conditions. Risk factors for diseases negatively influenced by vasospasm and other forms of vasoconstriction or abnormal vasodilatation, such as diabetic retinopathy, migraine, peripheral vascular disease, disorders of the microcirculation of the optic nerve, low tension or normal tension glaucoma, chronic open angle or primary open angle glaucoma, coronary artery disease, ischemic heart disease, ischemic cerebrovascular disease and systemic hypertension, are reduced by the dosage form of this invention by virtue of the action of elemental magnesium as a physiological calcium channel blocker and its action in reducing activating factors which are involved in the production of inflammatory, vasospastic cytokines, in addition to the complementary actions of the other described components of the dosage form.

Since a major diagnostic feature of glaucoma is a progressive hypovascular atrophy of the optic nerve and consequent loss of the visual field, the present invention is particularly useful as therapy for glaucoma. The measurement of the profundity and frequency of vasospastic incidents, for example by laser Doppler measurements, has proven to be a useful diagnostic predictor of the probability of developing glaucomatous visual field loss. The present invention, due to its ability to influence vascular smooth muscle tone and vasoconstriction, is useful for treating vasospasm and for reducing this risk factor.

An additional example of the utility of this invention to control risk factors is found in the influence of magnesium and the other components of the dosage form upon lipid metabolism in atherosclerosis and diseases of the circulatory system. The formation and presence of oxidized low density lipids ((ox)LDL) in vascular tissue is closely congruent with certain manifestations of endothelial cell damage leading to endothelial dysfunction, such as: (1) arterial vasospasm resulting from the release of the powerful vasoconstrictor endothelin-1 and other activating factors (e.g., Platelet Activating Factor) involved with the inflammatory cytokines; (2) proliferation of microvascular smooth muscle fibers and hypertrophy from repetitive or prolonged vasospasm, which reduces the vascular lumen; (3) activation and increased adhesiveness of platelets and white blood cells leading to turbulence and obstruction of blood flow through the lumen of small vessels which, in turn, promotes the development of atherosclerotic plaque, embolism and thrombosis; (4) production of ox(LDL)-induced lipid filled "foam cells" which are additional precursors of progressive vascular atherosclerosis. Administration of the compositions and dosage forms of the invention reduces the risk of dysfunctional endothelial cascade and reduces the risk of progressive generalized atherogenesis. As a result, risk factors for cardiovascular disease such as heart attack, stroke and hypertension are reduced.

All diseases which independently cause microvasculopathy, such as diabetes mellitus (diabetic retinopathy, peripheral vascular failure, nephropathy and cardiopathy, among others) and alcoholism, and others which are worsened by vasospasm and the other cellular processes mentioned above, benefit by the reduction of these risk factors. Specifically the reduction of sorbitol, a major metabolic by-product of glucose, reduces the risk of the many vascular conditions which complicate diabetes mellitus. In summary, the present invention is useful in reducing microvasculature-related risk factors that are clinically present in other diseases that are primarily caused by or worsened by the vascular pathologies described above and which are often associated with exaggerated vasoconstriction and its counterpart, abnormal vasodilatation.

The foregoing is offered primarily for purposes of illustration. It will be readily apparent to those skilled in the art that the proportions, materials, formulation procedures, administration protocols and other parameters of this invention may be further modified or substituted in various ways without departing from the spirit and scope of the invention.

We claim:

1. A unit dosage form for treatment of vasoconstriction and physiological conditions giving rise thereto, said dosage form consisting essentially of a combination of the following components in therapeutically effective amounts as the only active ingredients therein:

(i) one or more magnesium compounds;

(ii) a member selected from the group consisting of α-tocopherol, β-tocopherol, and esters thereof;

(iii) a member selected from the group consisting of ascorbic acid and ascorbate ion;

(iv) a member selected from the group consisting of folic acid and folate ion; and (v) selenium.

2. A unit dosage form in accordance with claim 1 in which said components are in the following ranges of amounts:

(i) about 20 mg to about 700 mg;

(ii) about 15 IU to about 1,000 IU;

(iii) about 30 mg to about 1,000 mg;

(iv) about 0.05 mg to about 0.225 mg; and (v) about 0.005 mg to about 0.15 mg.

3. A unit dosage form in accordance with claim 1 in which said components are in the following ranges of amounts:

(i) about 40 mg to about 180 mg;

(ii) about 20 IU to about 400 IU;

(iii) about 40 mg to about 500 mg;

(iv) about 0.10 mg to about 0.20 mg; and (v) about 0.005 to about 0.035 mg.

4. A unit dosage form in accordance with claim 1 in which the weight ratios of components (ii), (iii), and (iv) relative to component (i) are in the following ranges:

(ii) about 0.2:1 to about 2:1;

(iii) about 0.2:1 to about 2:1; and (iv) about 0.0003:1 to about 0.0030:1.

5. A unit dosage form in accordance with claim 1 in which the weight ratios of components (ii), (iii), and (iv) relative to component (i) are in the following ranges:

(ii) about 0.5:1 to about 1:1;

(iii) about 0.5:1 to about 1:1; and (iv) about 0.00075:1 to about 0.0020:1.

6. A unit dosage form in accordance with claim 1 in which component (i) is one or more members selected from the group consisting of magnesium lactate, magnesium citrate, magnesium stearate, magnesium acetate, magnesium ascorbate, magnesium malate, magnesium orotate, magnesium diglycinate, and magnesium oxide.

7. A unit dosage form in accordance with claim 1 in which component (i) is a combination of magnesium compounds comprising magnesium citrate and magnesium ascorbate.

8. A unit dosage form in accordance with claim 1 in which component (i) is a combination of magnesium compounds comprising magnesium acetate, magnesium citrate, and magnesium oxide.

9. A unit dosage form in accordance with claim 1 in which component (i) is a combination of magnesium compounds comprising magnesium lactate, magnesium acetate, magnesium citrate, magnesium ascorbate, and magnesium oxide.

10. A unit dosage form in accordance with claim 1 in which component (ii) is a member selected from the group consisting of α-tocopherol, α-tocopherol acid succinate, and α-tocopherol acetate.

11. A unit dosage form in accordance with claim 1 in which said components are formulated as a member selected from the group consisting of a tablet, a gelatin capsule, a solution, a suspension, and a powder.

12. A unit dosage form in accordance with claim 1 in which said components are formulated as a substantially homogeneous tablet that releases all of said components into the stomach upon ingestion for contact with gastric fluid.

13. A unit dosage form in accordance with claim 12 in which said components are:

(a) magnesium oxide, (b) magnesium acetate, (c) magnesium ascorbate, (d) α-tocopherol succinate, (e) folic acid, and (f) selenium.

14. A unit dosage form in accordance with claim 13 in which said components are:

(a) magnesium oxide, (b) magnesium acetate, (c) magnesium ascorbate, (d) magnesium citrate, (e) α-tocopherol succinate, (f) folic acid, and (g) selenium.

15. A unit dosage form in accordance with claim 14 in which components (a) through (g) are present in the following ranges of amounts (a) about 50 mg to about 100 mg, (b) about 40 mg to about 100 mg, (c) about 50 mg to about 100 mg, (d) about 150 mg to about 250 mg, (e) about 50 IU to about 100 IU, (f) about 0.03 mg to about 0.3 mg, and (g) about 0.007 mg to about 0.02 mg.

16. A unit dosage form in accordance with claim 13 in which components (a) through (f) are present in the following ranges of amounts:

(a) about 50 mg to about 100 mg, (b) about 40 mg to about 100 mg, (c) about 150 mg to about 250 mg, (d) about 50 IU to about 100 IU, (e) about 0.03 mg to about 0.3 mg, and (f) about 0.007 mg to about 0.02 mg.

17. A unit dosage form in accordance with claim 1 in which said components are formulated as a combination tablet in which said components are present as first and second portions separately formulated such that said first portion is released into the stomach upon ingestion for contact with gastric fluid, and said second portion is protected from release until reaching the intestine.

18. A unit dosage form in accordance with claim 17 in which the components of said second portion are coated with an acid-resistant protective coating that substantially prevents penetration thereof by gastric fluid but is penetrable by intestinal fluid.

19. A unit dosage form in accordance with claim 17 in which said components of said first portion are:

(a) a member selected from the group consisting of α-tocopherol, β-tocopherol, and esters thereof, (b) a member selected from the group consisting of folic acid and folate ion, (c) selenium, and (d) magnesium compounds;

and said components of said second portion are further magnesium compounds.

20. A unit dosage form in accordance with claim 17 in which said components of said first portion are:

(a) α-tocopherol succinate,
(b) folic acid,
(c) selenium,
(d) magnesium oxide,
(e) magnesium diglycinate, and
(f) magnesium ascorbate,
and said components of said second portion are:
(g) magnesium citrate, and
(h) magnesium acetate.

21. A unit dosage form in accordance with claim 20 in which components (a) through (h) are present in the following ranges of amounts:

(a) about 50 IU to about 100 IU,
(b) about 0.03 mg to about 0.3 mg,
(c) about 0.007 mg to about 0.20 mg,
(d) about 50 mg to about 100 mg,
(e) about 50 mg to about 200 mg,
(f) about 150 mg to about 250 mg,
(g) about 50 mg to about 100 mg, and
(h) about 40 mg to about 100 mg.

\* \* \* \* \*